(12) United States Patent
Ostrovsky et al.

(10) Patent No.: US 7,306,595 B2
(45) Date of Patent: Dec. 11, 2007

(54) SYSTEM AND METHOD FOR TISSUE ABLATION

(75) Inventors: Isaac Ostrovsky, Wellesley, MA (US); Jon T. McIntyre, Newton, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 32 days.

(21) Appl. No.: 10/993,306

(22) Filed: Nov. 18, 2004

(65) Prior Publication Data

US 2005/0107781 A1 May 19, 2005

Related U.S. Application Data

(60) Provisional application No. 60/566,889, filed on Apr. 30, 2004, provisional application No. 60/523,225, filed on Nov. 18, 2003.

(51) Int. Cl.
*A61B 18/18* (2006.01)
(52) U.S. Cl. .................................. 606/41; 607/101
(58) Field of Classification Search ............ 606/32–52; 607/101–102; 128/898
See application file for complete search history.

(56) References Cited

U.S. PATENT DOCUMENTS

| | | | |
|---|---|---|---|
| 4,627,444 A | 12/1986 | Brooker et al. | |
| 5,007,908 A * | 4/1991 | Rydell ....................... | 606/47 |
| 5,156,609 A | 10/1992 | Nakao et al. | |
| 5,277,201 A | 1/1994 | Stern | |
| 5,403,311 A | 4/1995 | Abele et al. | |
| 5,458,597 A * | 10/1995 | Edwards et al. ............... | 606/41 |
| 5,507,743 A | 4/1996 | Edwards et al. | |
| 5,782,827 A | 7/1998 | Gough et al. | |
| 5,807,395 A | 9/1998 | Mulier et al. | |
| 5,827,276 A * | 10/1998 | LeVeen et al. ................ | 606/41 |
| 5,964,754 A | 10/1999 | Osypka | |
| 5,980,517 A | 11/1999 | Gough et al. | |
| 5,980,563 A | 11/1999 | Tu et al. | |
| 6,090,105 A * | 7/2000 | Zepeda et al. ................ | 606/41 |
| 6,280,441 B1 | 8/2001 | Ryan | |
| 6,451,016 B1 | 9/2002 | Sarkis | |
| 6,497,704 B2 | 12/2002 | Ein-Gal | |
| 6,837,884 B2 * | 1/2005 | Woloszko ..................... | 606/32 |

(Continued)

FOREIGN PATENT DOCUMENTS

WO 00/32129 6/2000

(Continued)

*Primary Examiner*—Michael Peffley
(74) *Attorney, Agent, or Firm*—Vista IP Law Group LLP

(57) ABSTRACT

A tissue ablation device comprises first and second electrodes of opposite polarities, the first electrode being mounted to a first elongated member for movement relative to the second electrode for separation therefrom by a desired distance. A method of ablating a tissue comprises inserting first and second electrodes to desired initial positions relative to a tissue mass to be ablated and applying electrical energy to the first and second electrodes to ablate a first portion of tissue between the first and second electrodes in combination with the step of applying electrical energy to desired second positions separated from the desired initial positions by a distance selected to transfer electrical energy around the first portion of tissue through a second portion of tissue to be ablated, the second portion of tissue surrounding the first portion of tissue.

14 Claims, 13 Drawing Sheets

U.S. PATENT DOCUMENTS

| | | |
|---|---|---|
| 6,869,430 B2 * | 3/2005 | Balbierz et al. ............... 606/41 |
| 6,889,089 B2 * | 5/2005 | Behl et al. .................... 607/99 |
| 6,958,064 B2 | 10/2005 | Rioux et al. |
| 2002/0022864 A1 | 2/2002 | Mahvi et al. |
| 2002/0147446 A1 | 10/2002 | Ein-Gal |
| 2004/0147828 A1 * | 7/2004 | Gibson ....................... 600/374 |
| 2004/0158239 A1 * | 8/2004 | Behl et al. .................... 606/41 |
| 2004/0267256 A1 | 12/2004 | Garabedian et al. |
| 2005/0080409 A1 | 4/2005 | Young et al. |
| 2005/0107781 A1 | 5/2005 | Ostrovsky et al. |

FOREIGN PATENT DOCUMENTS

| | | |
|---|---|---|
| WO | 00/66017 | 11/2000 |
| WO | 02/22032 | 3/2002 |
| WO | 02/053036 | 7/2002 |

* cited by examiner

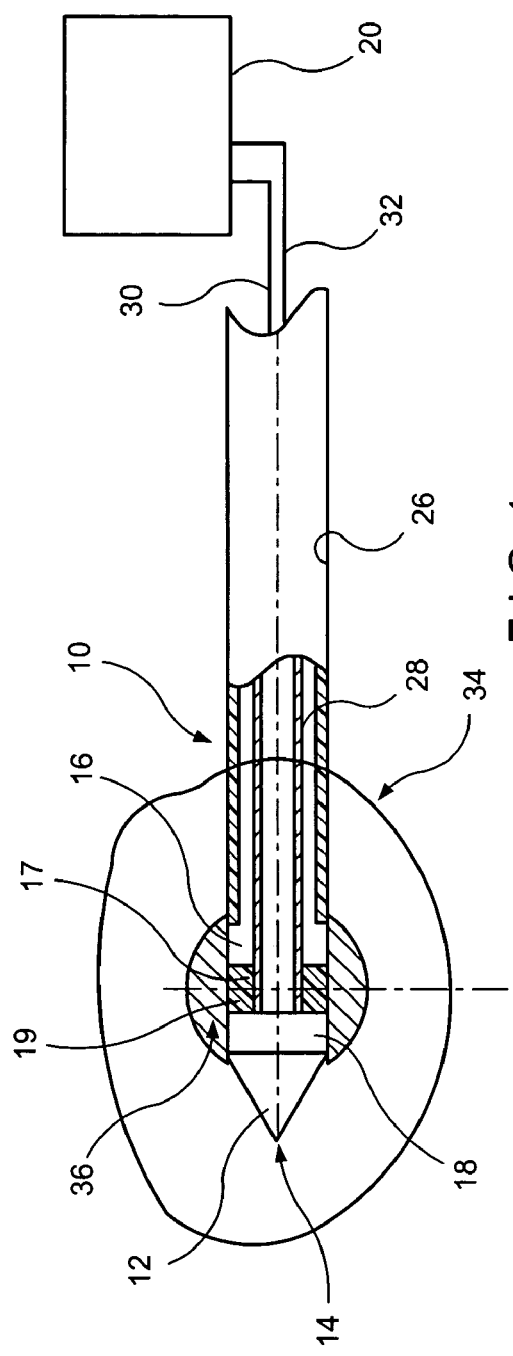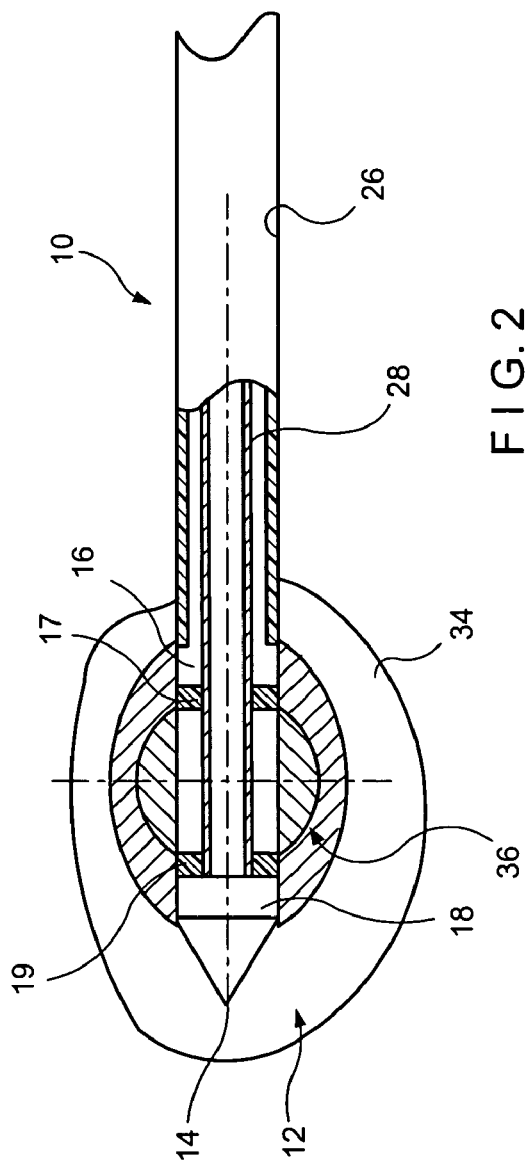

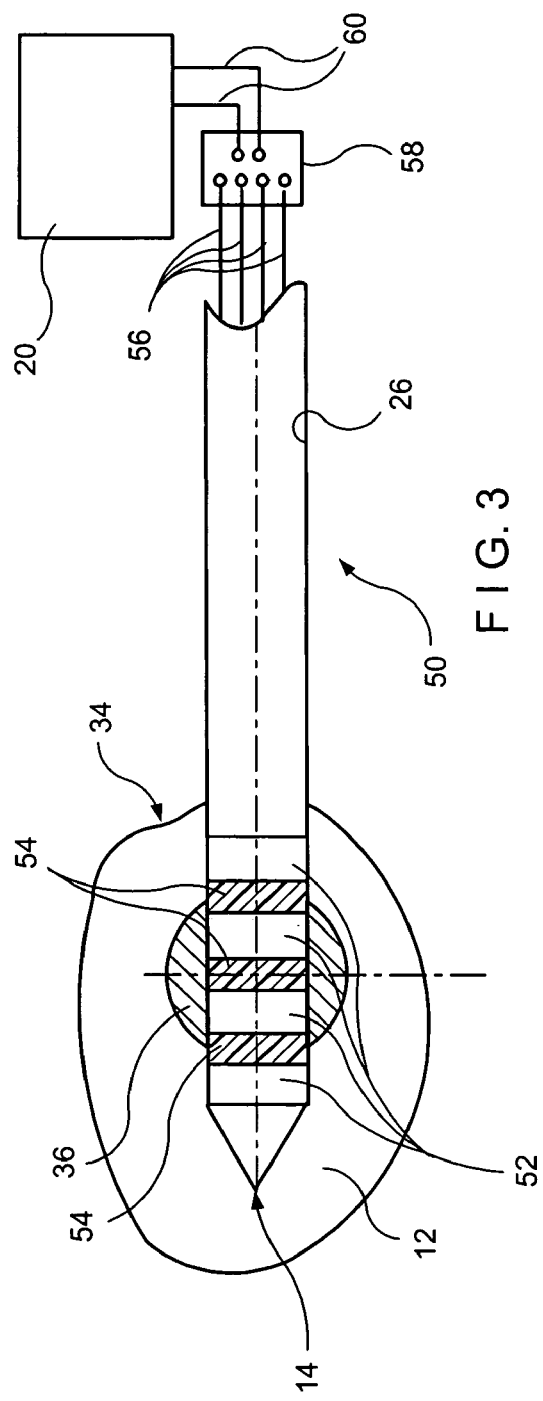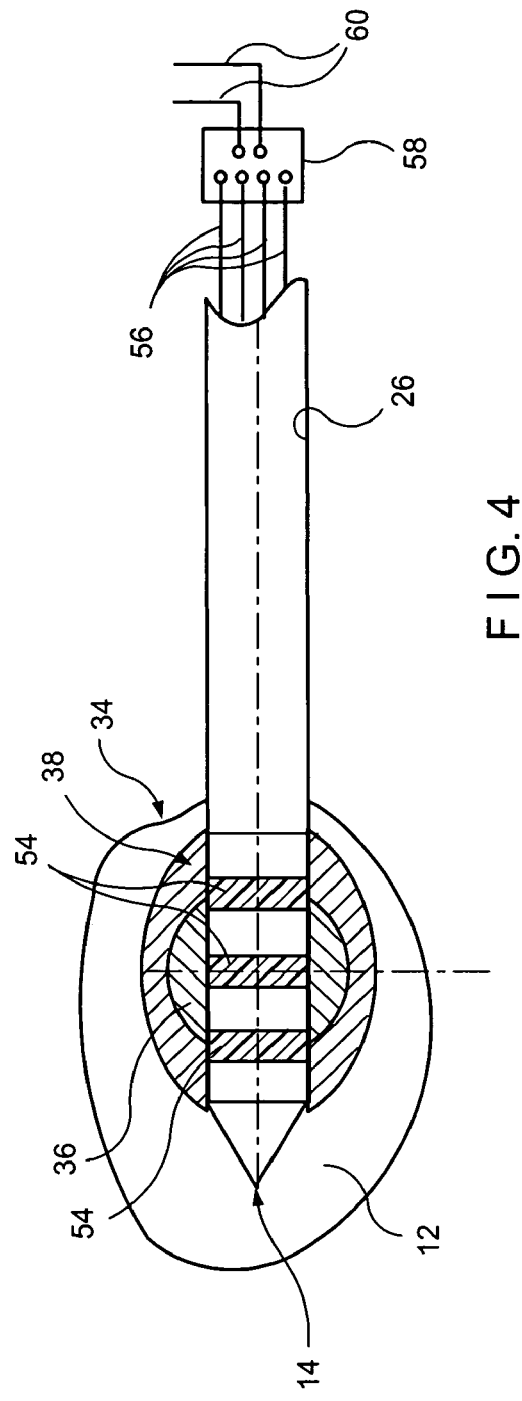

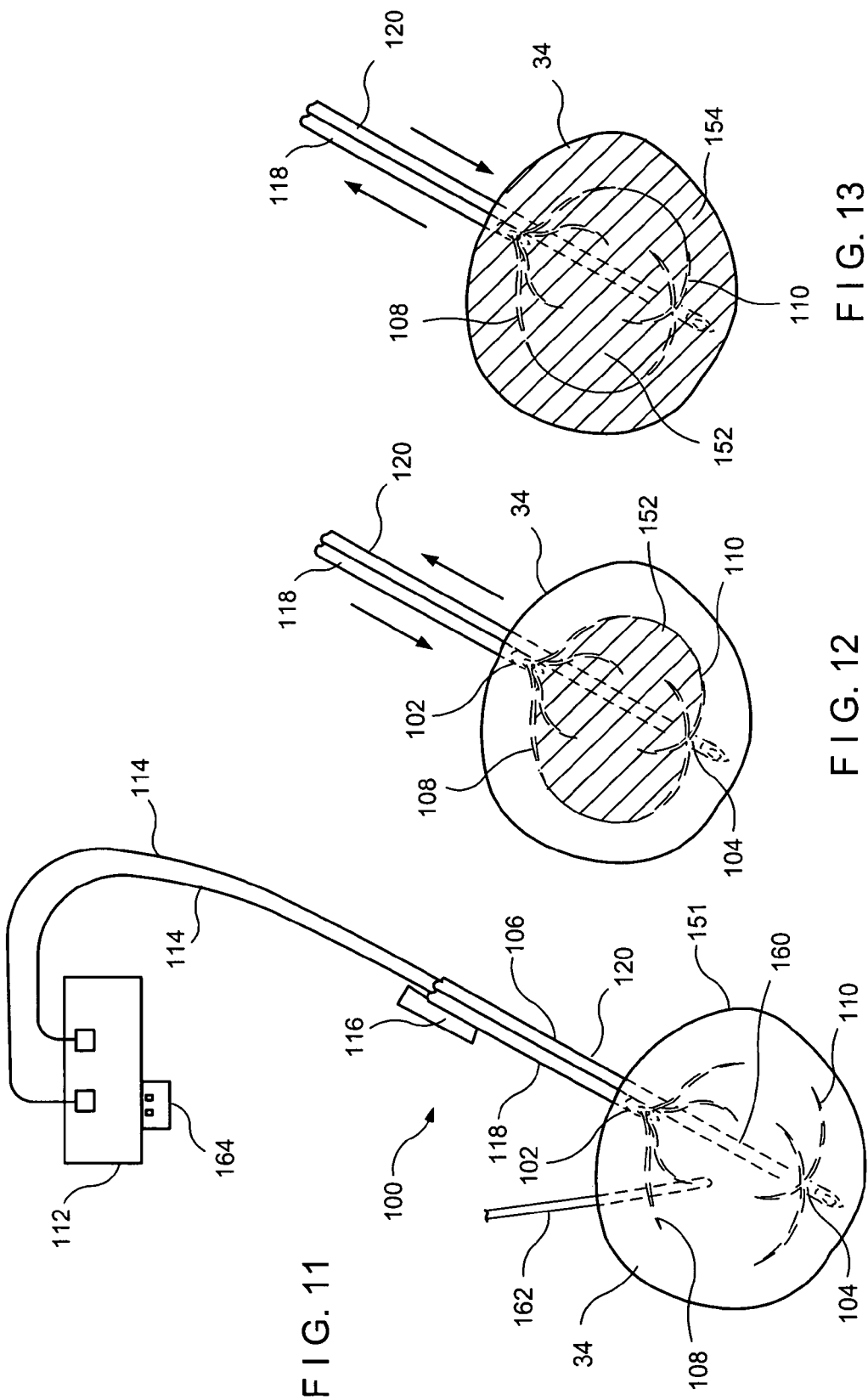

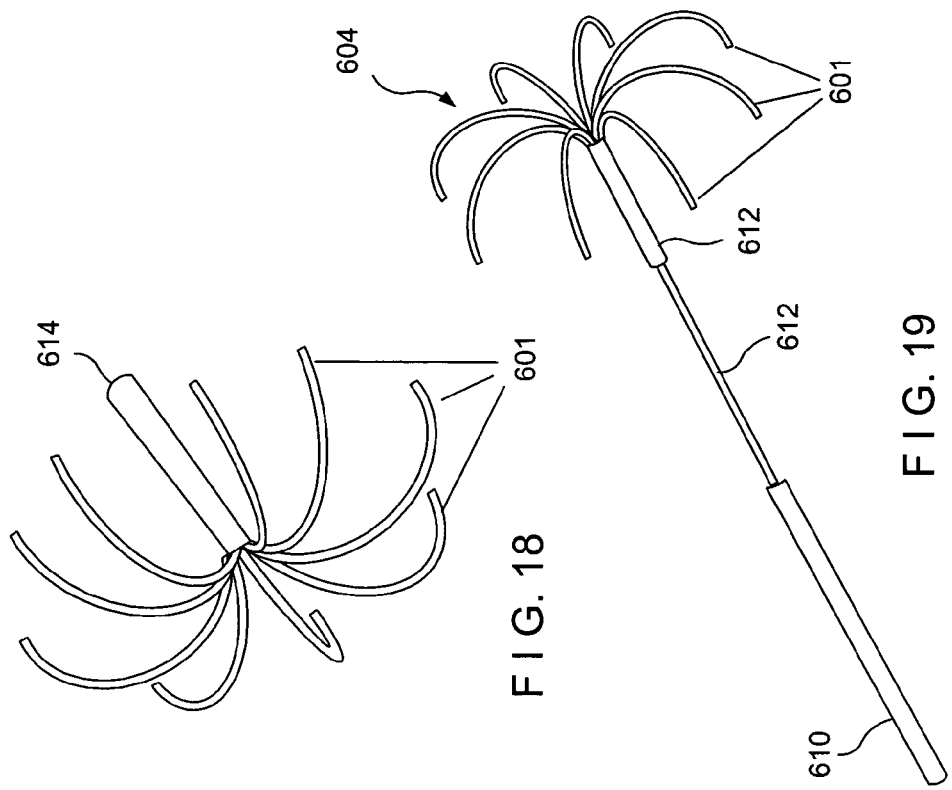
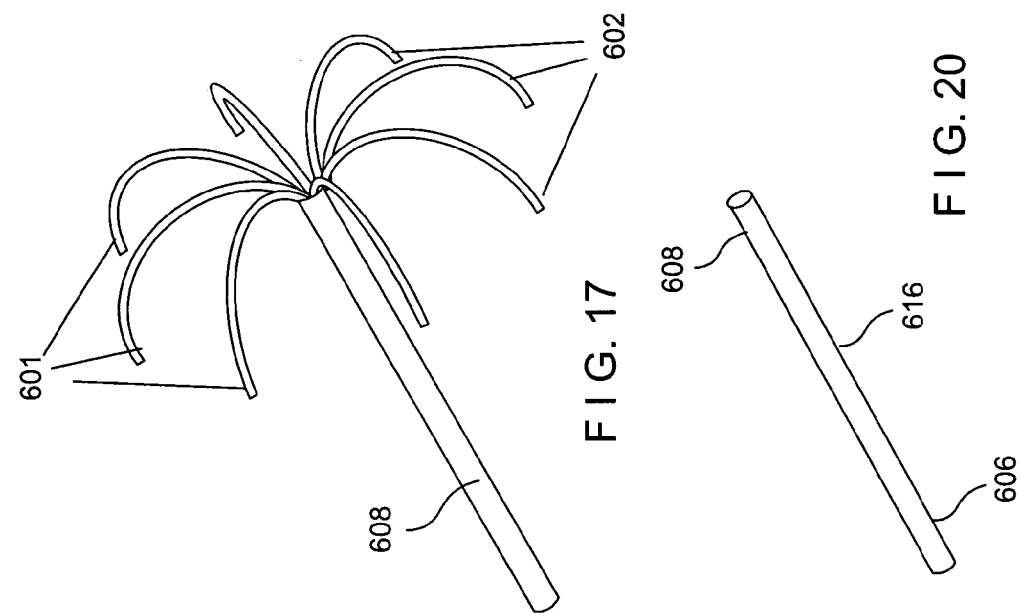

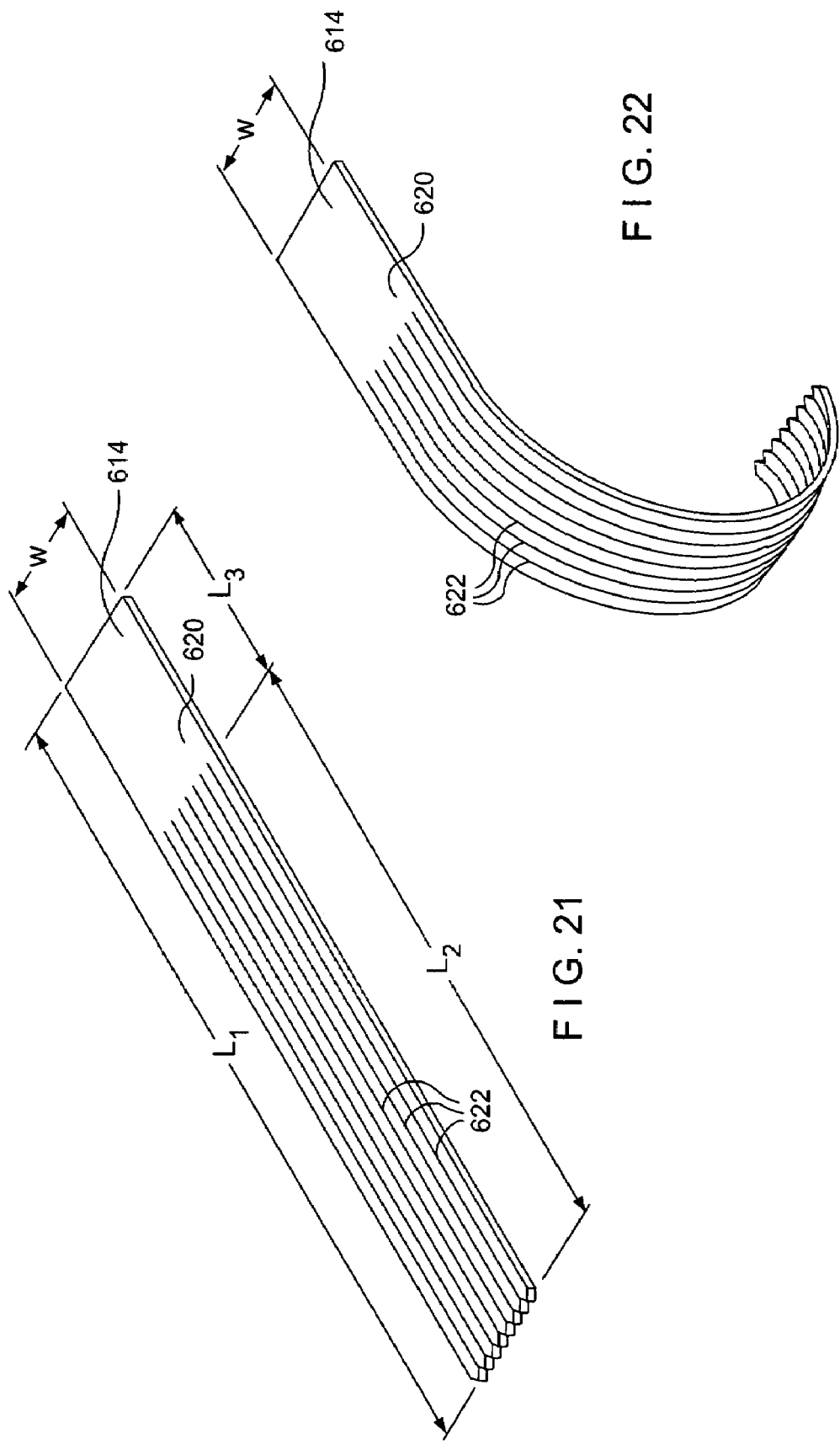

SYSTEM AND METHOD FOR TISSUE ABLATION

CLAIM TO PRIORITY

Priority is claimed to U.S. Provisional Patent Application Ser. No. 60/523,225, filed Nov. 18, 2003, entitled "RF Ablation and Fixation Device" and U.S. Provisional Patent Application Ser. No. 60/566,889, filed Apr. 30, 2004, entitled "SYSTEM AND METHOD FOR RADIO FREQUENCY TISSUE ABLATION." The entire disclosures of these prior applications are considered part of the disclosure of the accompanying application and are hereby incorporated by reference herein.

BACKGROUND INFORMATION

The treatment of abnormal tissue masses (e.g., fibroids and tumors) which grow in proximity to healthy tissue often involves the destruction of tissue. For example, local ablation of a tissue mass may be carried out by inserting a therapeutic device thereinto to destroy the targeted cells. For example, electrical energy may be applied to the tissue mass by placing one or more electrodes into the tissue mass and discharging electric current therefrom to ablate the tissue. Alternatively, fluids with appropriate properties may be injected into the vicinity of the tissue mass to chemically necrose selected portions of tissue.

When electric energy is used to ablate tissue, the size and shape of the region of tissue ablated depends, in part, on the configuration of the electrodes used for the procedure and, in part, on the strength of the charge applied. The energy received by the tissue dissipates rapidly as the distance from the electrode increases making it difficult to maintain a high level of energy density within a large volume of tissue. Therefore, the ablation of large tissue masses often requires a multi-step process with electrodes placed in an initial location for a first ablation and then re-inserted to a second location for further ablation with additional repetition of these steps as required. This increases the complexity and duration of the procedure with corresponding increases in patient discomfort and cost.

Another drawback of electrical ablation procedures is that the coupling between the tissue and the electrodes degrades as the procedure is carried out because, during the procedure, tissue in direct contact with the electrodes becomes desiccated and loses its conductivity. The electrodes thus become surrounded by high impedance tissue, preventing energy from reaching more distant tissue.

SUMMARY OF THE INVENTION

In one aspect, the present invention is directed to a tissue ablation device that comprises first and second electrodes of opposite polarities, the first electrode being mounted to a first elongated member for movement relative to the second electrode for separation therefrom by a desired distance. The present invention is also directed to a tissue ablation device comprising at least three electrodes mounted to an elongated member, each of the electrodes being electrically coupled to a corresponding electrical conductor, each of the conductors extending through the elongated member to a proximal end thereof for selective coupling to a source of electrical energy so that any desired combination of electrodes may be energized to ablate selected portions of tissue.

The present invention is further directed to a method of ablating a tissue comprising inserting first and second electrodes to desired initial positions relative to a tissue mass to be ablated and applying electrical energy to the first and second electrodes to ablate a first portion of tissue between the first and second electrodes in combination with the step of applying electrical energy to desired second positions separated from the desired initial positions by a distance selected to transfer electrical energy around the first portion of tissue through a second portion of tissue to be ablated, the second portion of tissue surrounding the first portion of tissue.

In the exemplary embodiments discussed below, the systems and methods are discussed in the context and with respect to applications (e.g., uterine fibroids) where sufficient energy is delivered to ablate the target tissue. However, it is contemplated that these systems and methods could be utilized in applications where various degrees of treatment of target tissue may be accomplished depending on the amount and duration of energy applied.

BRIEF DESCRIPTION OF DRAWINGS

FIG. 1 shows a partially cross-sectional view of a tissue ablation system according to a first embodiment of the present invention, in an initial configuration;

FIG. 2 shows the tissue ablation system of FIG. 1, in a second configuration;

FIG. 3 shows a tissue ablation system according to a second embodiment of the present invention during an initial phase of operation;

FIG. 4 shows the tissue ablation system of FIG. 3 in a second phase of operation;

FIG. 11 shows the tissue ablation system of FIG. 5 in a compression configuration;

FIG. 12 shows the tissue ablation system of FIG. 5 in an intermediate configuration;

FIG. 13 shows the tissue ablation system of FIG. 5 in an expansive configuration;

FIG. 17 shows a proximal array unit of the system of FIG. 16;

FIG. 18 shows an array for the system of FIG. 16;

FIG. 19 shows a distal array unit for the system of FIG. 16;

FIG. 20 shows a cannula along with a tube of the proximal array of the system of FIG. 16;

FIG. 21 shows a sheet of material for forming an array unit for the system of FIG. 16;

FIG. 22 shows the sheet of FIG. 21 with tines thereof bent to a deployed configuration;

DETAILED DESCRIPTION

Figure 5:
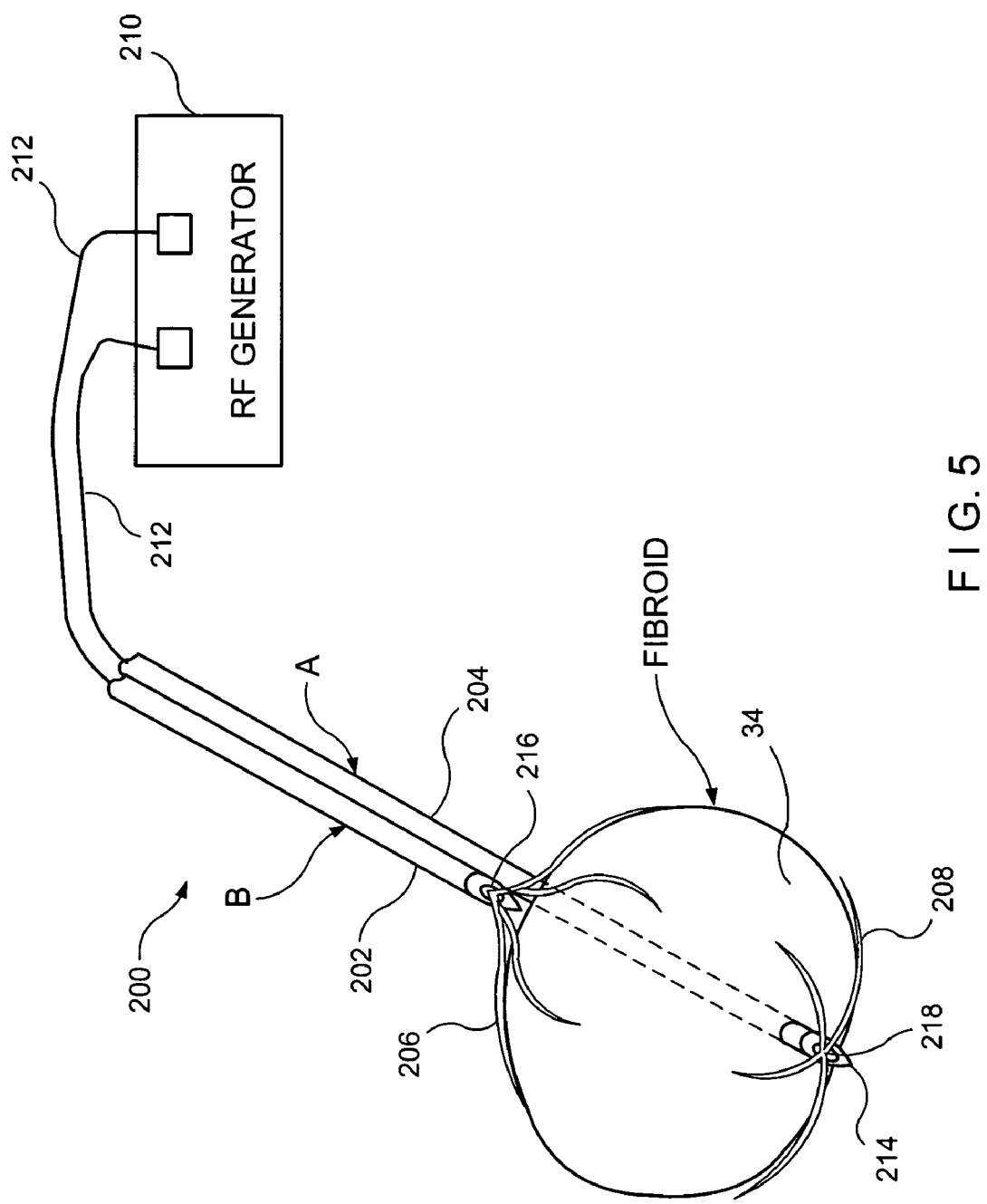
FIG. 5 shows a tissue ablation system according to a third embodiment of the invention in a first configuration.

The present invention may be further understood with reference to the following description and the appended drawings, wherein like elements are referred to with the same reference numerals. Embodiments of the present invention relate to methods and systems for treating (e.g., ablating) tissues within a patient's body. In particular, the embodiments are related to ablation of tissues using RF, or electric energy. In addition, although embodiments of this invention are described in conjunction with methods including multi-step ablation and other techniques, those skilled in the art will understand that these systems are all compatible with the single step ablation of sufficiently small target tissue masses.

Ablation of tissue is a common treatment for fibroids that develop on the walls of hollow organs and other abnormal tissue growths. For example, uterine fibroids are often treated by ablating the affected tissue using electrical energy, chemical compounds or other methods. During ablation treatment, a surgeon places one or more electrodes in contact with a target tissue mass and applies energy thereto to necrose the target tissue mass. In one type of procedure, electrodes are placed within the tissue, for example, by puncturing an outer surface of the target tissue mass.

Ablation treatments typically use electrodes which fall into one of two broad categories. Monopolar electrode systems use only one polarity of electrode which is inserted into the target tissue. An opposite polarity pad or other similar device is placed on the outer skin of the patient to provide a return path for the RF energy. A "loop" is thus formed, which includes the (usually positive) internal electrode, the target tissue mass and the (usually negative) pad. Bipolar electrode systems, on the other hand, use electrodes of both positive and negative polarity inserted in close proximity within the target tissue. Bipolar systems tend to be more efficient, since the two poles are both within the target tissue allowing a stronger concentration of energy to be delivered to the target tissue mass. Bipolar systems also allow the shape of the ablation region to be controlled more closely through targeted placement of the positive and negative electrodes.

Whether monopolar or bipolar systems are used, several problems may occur during RF ablation procedures. Since the intensity of the energy received by the tissue between the electrodes decreases rapidly with the distance from the electrodes, the volume of tissue which can be effectively ablated is limited. Specifically, RF energy intensity decreases in proportion to the square of the distance from the source. Thus, not far from the electrodes, the effect of this RF energy is considerably attenuated. In the past, ablation of a large volume of tissue has often required removing and repositioning the electrodes for a repeat of the treatment to expand on an initial ablation zone by creating a series of overlapping or abutting ablation zones. Alternatively, a plurality of devices were inserted simultaneously to create the overlapping or abutting ablation zones.

The inventors of the present system have noted that the coupling between the target tissue and the electrode(s) tends to degrade as the tissue in direct contact with the electrodes is desiccated by the ablation process, greatly reducing the conductivity of this tissue and blocking the transmission of RF energy to tissue further from the electrodes. This further limits the volume of tissue which may be ablated.

A first exemplary method according to the present invention addresses these issues through a multi-step process in which, after an initial ablation of a first core volume of tissue, energy is applied at different locations to ablate a second area surrounding this core volume to generate a larger ablated volume of tissue. Thereafter, additional portions of tissue surrounding this larger ablated volume of tissue may be ablated until a desired volume of tissue has been ablated. The method according to this embodiment of the invention will be described in conjunction with one or more exemplary systems for performing the method. However, those skilled in the art will understand that any of a variety of ablation systems may be used to perform the method.

Specifically, as shown in FIGS. 1 and 2, a system for tissue ablation according to a first embodiment of the invention includes an ablation probe 10 including a distal end 12 which may include a tissue penetrating tip 14. The probe 10 includes a first electrode 18 mounted adjacent a proximal end of the tip 14 with a second electrode 16 mounted on the tube 26 and separated from the first electrode 18 by first and second insulators 17, 19, respectively. For example, the tube 26 may be formed of an electrically insulative material with conductive materials forming the electrodes 16, 18 as would be understood by those skilled in the art.

As shown in FIG. 1, in an initial configuration, the first and second insulators 17, 19 abut one another while, in a subsequent configuration shown in FIG. 2, the first and second insulators 17, 19 are separated from one another (e.g., along an axis of the probe 10). Each of the electrodes 16, 18 is coupled to a source 20 of RF energy with the electrode 16 being coupled to a first pole of the source 20 and the electrode 18 coupled to a second pole with a polarity opposite that of the first pole. Thus the electrodes 16 and 18 form a bipolar ablation device. The electrode 16 is coupled to an outer tube 26 of the probe 10. An inner member 28, which may, for example, be formed of an electrically insulative material, extends within the outer tube 26 and passes through the insulator 17 to couple to the insulator 19 and the distal end 12. The inner tube 28 may be slid axially relative to the outer tube 26 to move the electrodes 16, 18 toward and away from one another between the initial and subsequent configurations. A first conductor 30 extends from the source 20 to the electrode 16, for example, through the outer tube 26, while a second conductor 32 extends from the source 20 to the electrode 18, for example, through the inner tube 28.

To perform an ablation using the probe 10, a user first penetrates a target tissue mass 34 using the distal tip 14 and, using known visualization techniques and devices, positions the probe 10 so that the electrodes 16, 18 are substantially centered within the tissue mass 34. The user then supplies RF energy to the electrodes 16, 18 from the source 20 to ablate a core region 36 immediately surrounding the electrodes 16, 18 within the tissue mass 34. The user continues to apply energy to the electrodes 16, 18 until a desired degree of ablation of the core region 36 has been achieved. As would be understood by those skilled in the art, the degree of ablation of the core region 36 may be monitored using known means by, for example, detecting the temperature and/or conductivity/impedance of the tissue.

When the desired degree of ablation of the core region 36 has been achieved, the user halts application of energy and slides the outer and inner tubes 26, 28 relative to one another until the electrodes 16, 18 are separated from one another by a desired distance. When the electrodes 16, 18 have been separated by the desired distance, the electrodes 16, 18 are energized once again and the energy flows around the non-conductive ablated tissue of the core region 36 to ablate a second region 38 surrounding the core region 36. The degree of ablation of this second region 38 is monitored as with the core region 36 and energy is applied to the electrodes 16, 18 until a desired degree of ablation of the second region 38 has been achieved. Then, if the target tissue mass 34 has still not been completely ablated as desired, the procedure may be iterated with the electrodes 16, 18 being separated by greater distances to ablate successive surrounding areas until the entire target tissue mass 34 has been ablated. Alternatively, the system may include a manual or automatic mechanism to incrementally increase the relative distance separating the electrodes 16, 18. Such mechanism may include some form of feedback loop which changes the distance depending on monitored parameters of the treatment or tissue (e.g., impedance, duration of applied energy and/or temperature) compared against a threshold or control value. Of course, those skilled in the art will understand that the size of the target tissue masses that may be ablated through this process will be limited as the length of the path the RF energy will need to travel between electrodes 16, 18 around the ablated tissue increases. The probe 10 has been used, for example, to ablate target tissue masses of approximately 1 to 8 cm in diameter and is most suitable for the ablation of tissue masses of approximately 2 to 4.5 cm in diameter.

A probe 50 according to a second embodiment of the invention is shown in FIGS. 3 and 4. The probe 50 includes four electrodes 52 separated from one another by insulators 54. Each of the electrodes 52 is connected to a corresponding conductor 56, with the conductors 56 being coupled to a switch 58 which is, in turn, coupled to the power source 20 via conductors 60. The switch 58 allows a user to supply power to any desired combination of the electrodes 52 so that power is applied at selected locations with respect to the target tissue mass 34 as will be described in more detail below. Those skilled in the art will understand that, although the probe 50 according to this embodiment is described with four electrodes 52, so long as there are at least three electrodes 52, any additional number and spacing of these electrodes may be employed to apply power at desired locations within a target tissue mass.

Specifically, the electrodes 52 are simply formed on the outer surface of the tube 26 by any known process with each of the corresponding conductors extending through the tube 26 to a proximal end thereof. As the electrodes 52 can be selectively energized in any combination (preferably in pairs), RF energy can be applied to selected locations within the target tissue mass 34 separated by pre-set selected distances to reproduce the ablation method described above in regard to the first system embodiment. Specifically, after the tissue penetrating tip 14 has entered the target tissue mass 34, the probe 50 is advanced until the middle electrodes 52 are centered therewithin. The two center electrodes 52 are then energized until the desired level of ablation has been achieved within the core region 36. Then the two outer electrodes 52 are energized to ablate the surrounding region 38. If, after the surrounding region 38 is ablated portions of the target tissue mass 34 remain unablated, the probe 50 may be repositioned to ablate the remaining portions. Of course, if a greater number of electrodes are provided along a greater length of the probe 50, the volume of tissue that may be ablated without repositioning the device will be increased. A feedback loop may be included with this embodiment, as described above, to automate the switching between combinations of electrodes.

According to third embodiment of the present invention, which is shown in FIG. 5, a tissue ablation device 200 provides an adjustable bipolar system where the distance between the electrodes can be easily changed and set by the surgeon to match the size of the fibroid being treated and/or to apply RF energy at various selected locations within a target tissue mass as described above. The apparatus according to this exemplary embodiment includes a pair of side by side elongated elements 202, 204 which may be formed, for example, as a pair of hollow needles. Each of the elongated elements 202, 204 comprises a channel 216, 218 containing an array of tines 206, 208, respectively. In addition, at least the elongated element 204 which extends further distally preferably includes a sharp point 214 adapted to pierce the target tissue mass 34.

Depending on the procedural needs of the operation, either one of the elongated elements 202, 204 may be deployed first by the surgeon. In cases where the target tissue mass 34 is located near a vital organ (e.g., a fibroid near the patient's intestine), it may be dangerous to immediately advance the needle 204 through the entire fibroid as there is a danger of puncturing the organ. In this case the needle 202 and the array 206 may be deployed first and may be pushed sufficiently into the target tissue mass 34 to at least partially stabilize the target tissue mass 34 and allow the surgeon to manipulate the position of the target tissue mass 34 using the needle 202. For example, the surgeon may move the target tissue mass 34 away from the vital organ, and create a safety space between the organ and the target tissue mass 34. Subsequently, the needle 204 may be advanced with a much reduced danger of inadvertently piercing the organ.

Once each of the needles 202 or 204 is in place, the arrays of tines 206, 208 may be deployed from the respective hollow channels 216, 218. The arrays of tines may, for example, be similar to those used in the LeVeen Needle Electrodes provided by Boston Scientific Oncology. In one embodiment the extension of the tines 206, 208 from the hollow channels 216, 218 may be controlled by the surgeon to match the general dimensions of the target tissue mass 34. The tines 206, 208 may also be designed to assume a specified shape upon being deployed from the needles 202, 204, for example, with a pre-set curvature corresponding to a shape of an outer surface of the target tissue mass 34 so that the tines 206, 208 can follow along this surface at or below the surface. For example, a shape memory material may be used to form the tines 202, 204 so that they will assume the desired shape as soon as they are deployed from the needles 202, 204.

After both needles and tines are deployed on or within the target tissue mass 34, each of the arrays of tines 206, 208 is connectable to a generator 210 to provide an electric potential therebetween. A current flow is thus induced through the target tissue mass 34 between the arrays of tines 206, 208, which heats and eventually destroys the tissue therebetween. In one embodiment, the impedance of the tissue between the electrodes (the arrays of tines 206, 208) is measured before RF energy is applied to provide a baseline against which the progress of the procedure may be measured. During the application of the current, the tissue's impedance is monitored, and the procedure may be terminated once a desired amount of change has occurred, corresponding to a certain ablation of the treated tissue. Alternatively, or in combination with impedance, the tissue's temperature may be monitored to control the procedure. Those skilled in the art will understand that such measures may be incorporated into any of the embodiments and/or methods described herein. Each of the arrays has a positive and negative polarity, respectively, forming a bipolar system. Each of the tines of an array can be activated together or in some combination of one or more tines in the array, in conjunction with similar control over the activation of tines in the other array, to accomplish various desired shapes of ablation volumes therebetween.

Figure 6:
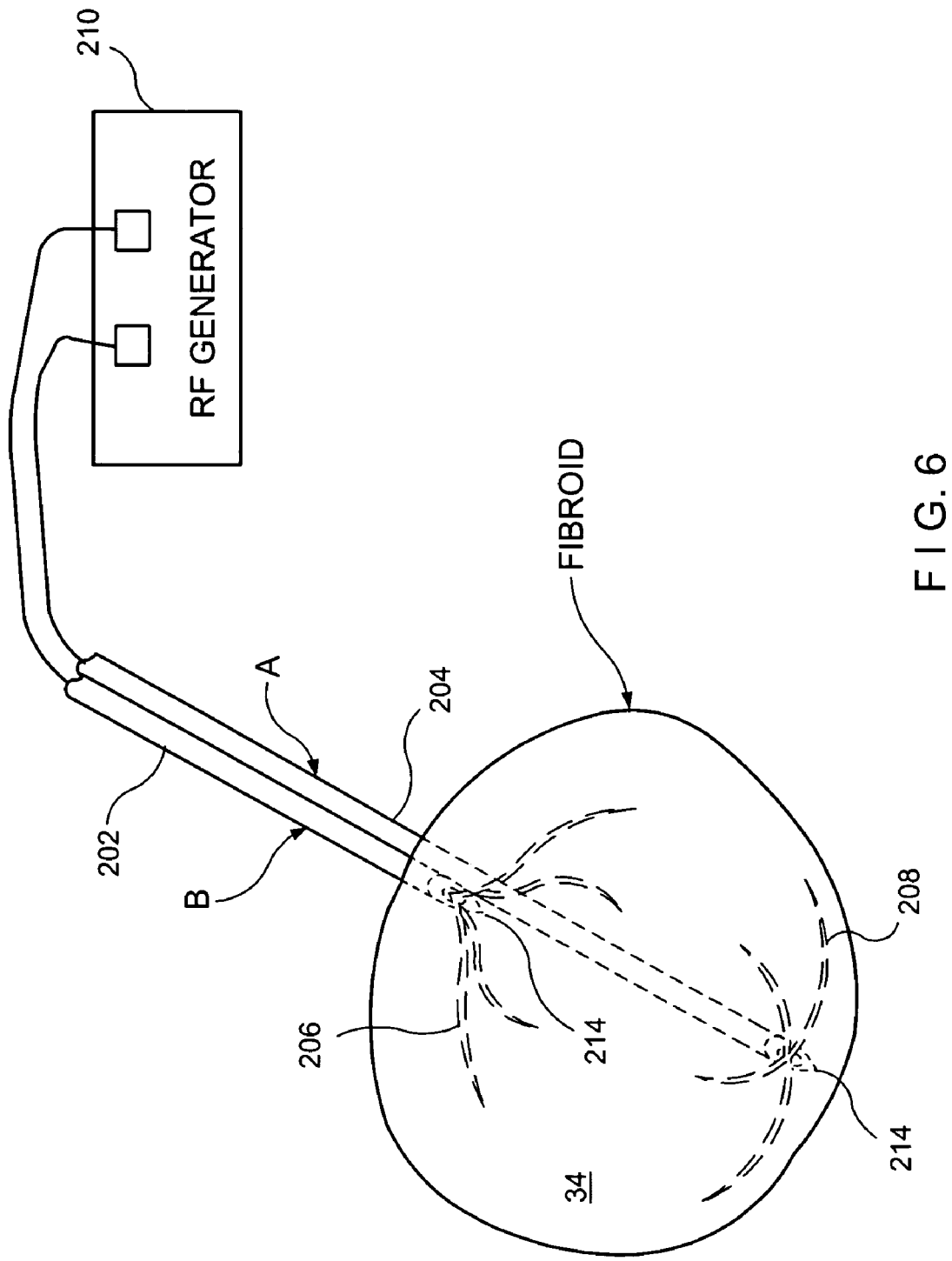
FIG. 6 shows the tissue ablation system of FIG. 5 in a second configuration.
Figure 8:
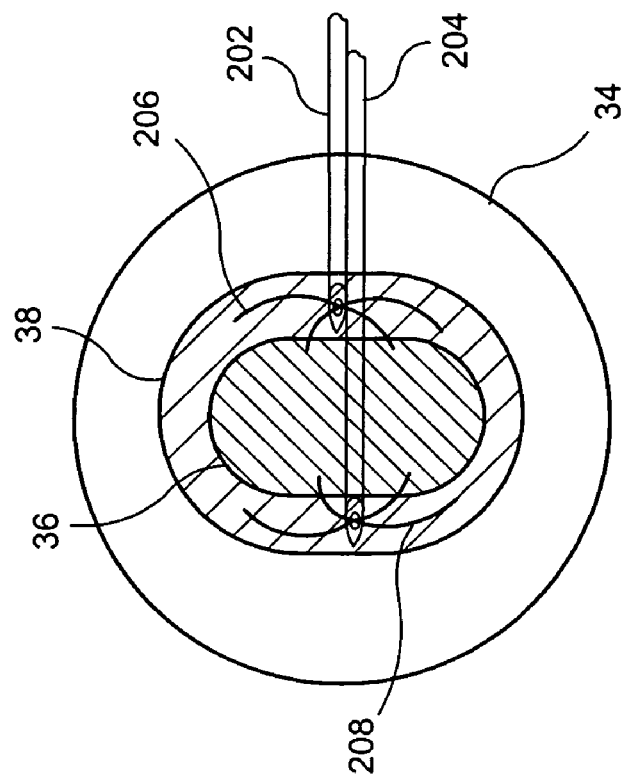
FIG. 8 shows the tissue ablation system of FIG. 5 in an second configuration of the multi-phase ablation process.

As described above, to carry out certain tissue ablation procedures, it may be advantageous to place the arrays of tines 206, 208 at one or more locations other than the surface of target tissue mass 34. Accordingly, as shown in FIG. 6, the needle 204 may be advanced into the target tissue mass 34 to a location below the surface thereof on a side opposite from the entrance puncture while the needle 202 is advanced into the tissue of the target tissue mass 34 only a small distance, so that its tip 214 is slightly below the surface of the target tissue mass 34. The arrays of tines 206, 208 may then be deployed at a selected depth within the target tissue mass 34. If necessary, either or both of needles 202, 204 may be advanced further or less into the target tissue mass 34, to carry out tissue ablation at a precise desired location.

Figure 7:
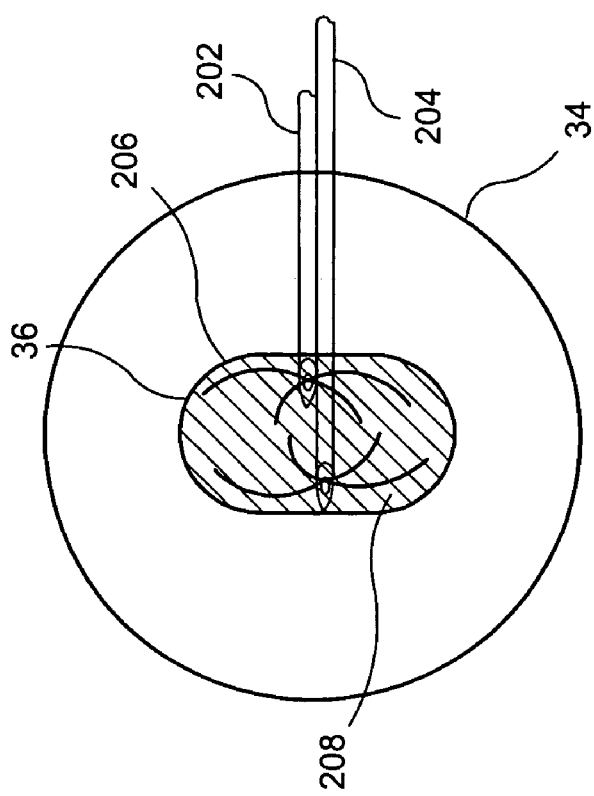
FIG. 7 shows the tissue ablation system of FIG. 5 in an initial configuration of a multi-phase ablation process.
Figure 10:
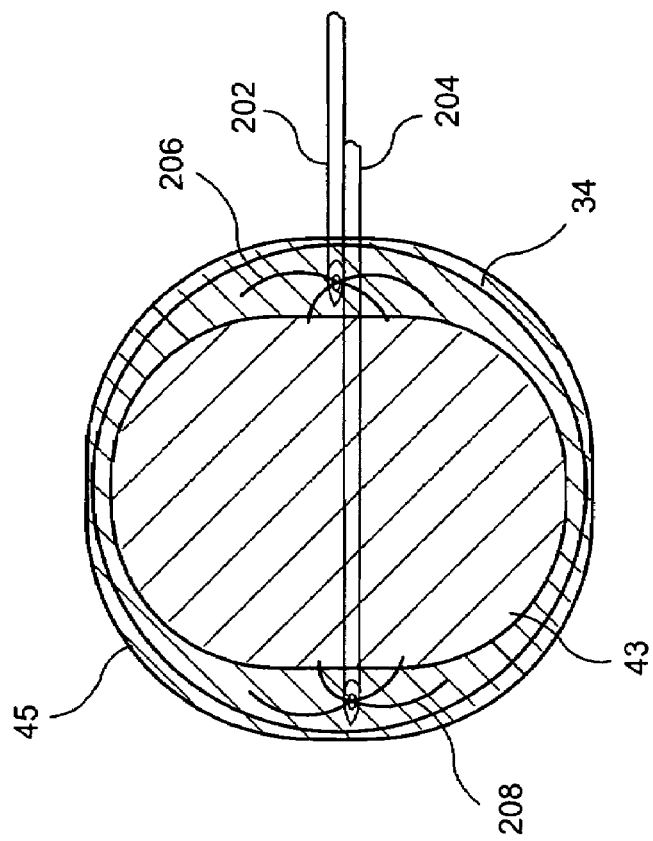
FIG. 10 shows the tissue ablation system of FIG. 5 in a fourth configuration of the multi-phase ablation process.
Figure 9:
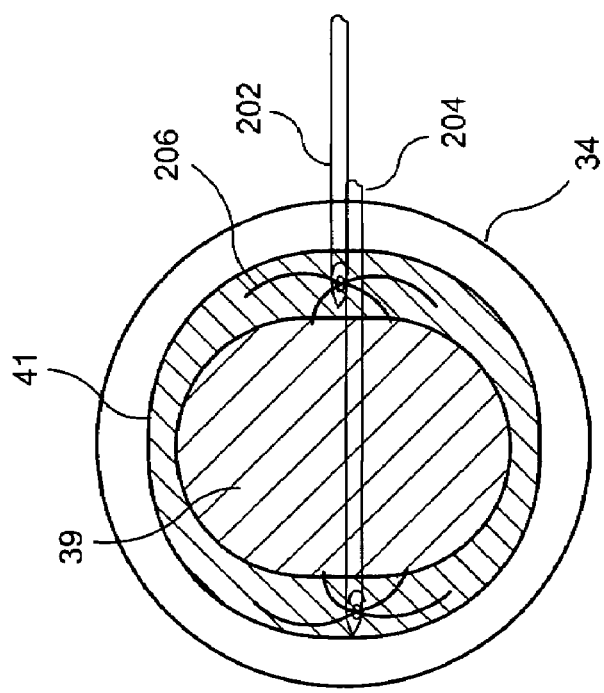
FIG. 9 shows the tissue ablation system of FIG. 5 in a third configuration of the multi-phase ablation process.

In addition, as shown in FIGS. 7-10, the device 200 may be employed to carry out a multi-step ablation process as described above in regard to the embodiments of FIGS. 1-4. To do this, the arrays 206, 208 are first positioned as shown in FIG. 7 around a central core region 36 of the target tissue mass 34 and energized until the core region 36 has been sufficiently ablated. After this core region 36 has been ablated to a desired degree, increasing its impedance, the arrays 206, 208 are moved to the location shown in FIG. 8 and energized. Energy is supplied to the arrays 206, 208 until ablation of a second region 38 surrounding the core region 36 reaches a desired level. This forms a larger high impedance mass 39 which includes the core region 36 and the second region 38. If the entire target tissue mass 34 has not yet been ablated, the arrays 206, 208 may be moved to the position shown in FIG. 9 to ablate a third surrounding region of tissue 41 as energy applied to the arrays 206, 208 flows around the high impedance mass 39 through the third region 41 to generate a larger high impedance mass 43. This process may be repeated again at a fourth location as shown in FIG. 10 until the entire target tissue mass 34 has been ablated to a desired degree by ablation of a fourth region 45.

As shown in FIG. 7, when using the device 200 or a similar device with arrays of tines, the arrays 206, 208 may preferably be positioned so that a distance between the arrays 206, 208 is less than an extent of the tines of the arrays 206, 208 away from the elongated elements 202, 204. This ensures that an extent of the core region 36 away from the elongated elements 202, 204 is greater than the diameter of the arrays 206, 208. Thus, iterations of the treatment will create subsequent treated regions of increasing width in this direction as the RF energy travels around the high impedance core. Thereafter, the iterations of the process described above will generate successively more spherical masses of ablated tissue until a distance separating the arrays 206, 208 exceeds the array diameter by a distance large enough that the ablated region begins to elongate in the axial direction. This method increases the maximum volume of tissue that can be treated with an array of a certain size.

For a two step process, for example, using arrays 206, 208 of approximately 2 cm diameter, a distance between the array 206 and the array 208 was set at approximately 5 mm in the initial configuration. After a desired degree of ablation was achieved in this initial configuration, the desired distance between the arrays 206, 208 was moved to approximately 15 mm in the second configuration. The arrays 206, 208 were then energized to treat the second region 38. Using these distances, a high impedance mass 39 having a width (i.e., distance in a direction perpendicular to axes of the elongated elements 202, 204) of approximately 40 mm in diameter was ablated.

For a three step process, using arrays 206, 208 of approximately 2 cm diameter, a distance between the array 206 and the array 208 was set at 5 mm in the initial configuration. After a desired degree of ablation has been achieved in the core region 36 in this initial configuration, the desired distance between the arrays 206, 208 was moved to approximately 13 mm in the second configuration. The arrays 206, 208 were then energized to treat the second region 38. After the second region 38 was sufficiently treated, the arrays 206, 208 were then moved to a third position separated from one another by approximately 23 mm. Using these distances, a high impedance mass having a width (i.e., distance in a direction perpendicular to axes of the elongated elements 202, 204) of approximately 40 mm and a length (i.e., distance substantially parallel to the axes) of approximately 45 mm was ablated. Thus, a device having arrays with a diameter of 2 cm may be used to ablate target tissue masses of twice that size or greater.

In addition, ablation results may be improved by applying compressive and expansive forces to various portions of the target tissue via the electrodes. To compress the tissue, the distance between the electrodes and a large portion of the target tissue is reduced, so that a high RF energy intensity is maintained. In addition, different regions of the target tissue are treated separately, so that desiccation of tissue adjacent to the electrodes in one region does not reduce the effectiveness of the treatment in other regions of the target tissue.

More specifically, the distribution of RF energy throughout the target tissue may be improved by placing electrodes closer to one another within a given volume of tissue to be ablated. Moving the electrodes together after the electrodes have been deployed within tissue in its natural, uncompressed, state, for example, reduces the distance between the electrodes and increases the intensity of the RF energy received by the tissue compressed therebetween. The dimensions of the lesion formed by the treatment in the target tissue may also be increased through a dual mode ablation procedure including a first mode of ablation during which a volume of tissue between the electrodes is ablated and a second mode of ablation in which a volume of tissue located external to the electrodes is ablated.

FIGS. 11-13 show a bipolar RF ablation device 100 similar to that described above for use in the treatment of target tissue masses 34 (e.g., tumors and fibroids). In particular, the device 100 may be used to ablate uterine fibroids after insertion into the uterus through the patient's cervix. The low profile of the device may also allow it to be inserted percutaneously (such as in laparoscopic procedures) into the uterus through the abdominal wall with a minimal amount of punctures. In this embodiment, the ablation device 100 is a bipolar device including positive and negative electrodes 102, 104. The two electrodes 102, 104 may be placed at the distal end of a shaft 106 which may include a handle portion to allow the surgeon to place the electrodes in proximity to a target tissue mass 34 (e.g., a tumor, uterine fibroid, or any other abnormal tissue). The shaft 106 may be further divided into a first shaft 118 and a second shaft 120, with the first shaft 118 connected to the electrode 102 and the second shaft 120 connected to the electrode 104. The location of the two electrodes may be interchangeable, i.e. either the positive or negative electrode may be more proximal relative to the shaft 106.

In the exemplary embodiment, the first and second shafts 118, 120 are slidable relative to each other, so that the distance between positive and negative electrodes 102, 104 may be changed during the procedure. For example, a control portion 116 may be provided, to allow the user to manually slide the shafts 118, 120 relative to one another changing the distance between the electrodes 102, 104. In a different embodiment, other mechanisms may be used to move the electrodes 102, 104 relative to one another. For example, one or more springs may be used to assist in positioning the electrodes 102, 104 as desired. Alternatively, pneumatic or hydraulic power may be used to achieve or control the movement of the electrodes 102, 104 as they are displaced to compress selected portions of the target tissue mass 150. In different embodiments, piezoelectric actuators or other electric actuators may be utilized to move the electrodes 102, 104 relative to one another and to provide and maintain the desired tissue compression. As would be understood by those skilled in the art, the current distance between the electrodes 102, 104 could be indicated by visible markers on the shafts 118 and 120 or mechanical indexing at the handle could control and indicate distance between the electrodes 102, 104. In addition, in this embodiment and others described herein visible or radiopaque markers may be included on the shaft to indicate a depth of penetration of the shaft into the target tissue mass 34.

The first and second elongated shafts 118, 120 may be co-linear and may be slidably connected along a longitudinal axis of the shaft 106. In this manner, the electrodes 102, 104 may be translated longitudinally relative to one another. It will be apparent to those of skill in the art that other configurations of the shaft 106 may be employed. For example, the first and second shafts 118, 120 may be coaxial, or may be rotationally coupled to one another. Alternatively, the shaft 106 may comprise a single member which separates into multiple shafts near a distal end thereof to support separate electrodes. In another alternative embodiment, the shaft 106 may comprise a single member with a distal end supporting hinged or slidable electrodes, as well as a mechanism to vary the distance between those electrodes. Automated mechanisms in conjunction with feedback loop control, as described above, could be included in these embodiments as well.

As would be understood by those skilled in the art, the RF energy applied to the target tissue mass 34 may be produced by an RF generator 112 or by a similar device. A battery, a generator or a device utilizing an external power supply may be used to power the RF ablation device 100 with the current provided by the generator 112 reaching the electrodes 102, 104 via connection lines 114 and/or through conductive components of the first and second shafts 118, 120. It will be apparent to those of skill in the art that the RF generator 112 may comprise any suitable source of electrical energy which is appropriate for medical tissue ablation.

In the exemplary embodiment shown in FIG. 11 the positive and negative electrodes 102, 104 comprise arrays of tines 108, 110 which extend, respectively, therefrom. The arrays of electrode tines 108, 110 may be deployed after the shaft 106 has pierced an outer surface 151 of the target tissue mass 34 placing the respective electrodes 102, 104 within the target tissue mass 34. For example, the deployed arrays 108, 110 may form two umbrella-like structures which generally delimit portions of the target tissue mass 34 which will be affected by the RF energy.

According to the present invention, after they have been deployed in the target tissue mass 34, the distance between the electrodes 102, 104 may be varied to selectively press the electrodes against different regions of the target tissue mass 34 therearound. The variable distance feature provides for a dual mode array of electrodes, which selectively favors the application of the RF energy to different regions of the target tissue mass 34. For example, when the electrodes 102, 104 are moved nearer to each other after deployment in the configuration shown in FIG. 11, the region of tissue 152 located between the electrode arrays 108, 110 is compressed by inward facing surfaces of the electrode arrays 108, 110 as they press against the outer portions of the tissue region 152. (See FIG. 12). In this first mode of operation of the RF ablation device 100, energy transfer between the electrode arrays 108, 110 and the inner region of tissue 152 is favored. The improved contact between the electrodes 102, 104 and the tissue of the region 152 increases the energy coupling with that target tissue, and favors absorption of most of the RF energy by the tissue located between the electrode arrays 108, 110.

The first mode of operation of the RF ablation device 100 described above thus provides a greater energy intensity through the target tissue portion 152, located between the electrode arrays 108, 110. By moving the electrodes 102, 104 towards one another, and by compressing the tissue therebetween, the distance through the tissue from one electrode to the other is reduced. Less attenuation of the RF energy through the tissue takes place, since the energy travels a smaller distance from the electrodes. The treatment to ablate a specified volume of tissue may thus require less time or a lower energy output from the generator 112.

In a second mode of operation, the positive and negative electrode arrays 108, 110 may be translated away from one another after deployment (or, e.g., after application of RF energy to compressed tissue in the first mode of operation) to apply an expansive force to the tissue. The increased separation causes the outer surfaces of the electrode arrays 108, 110 to press more strongly against the inner portion of the region of tissue 154 surrounding the outside of the electrode arrays 108, 110. (See FIG. 13). Because of the pressure applied between the electrodes 102, 104 (and thus the electrode arrays 108, 110) and the surrounding tissue region 154, a greater energy coupling is established with the target tissue in the surrounding region 154. As a result, this mode of operation of the RF ablation device 100 favors absorption of RF energy by the target tissue in the region 154. In addition, some compression of the tissue in the region 154 also takes place, due to the displacement of electrode arrays 108, 110. Accordingly, a larger volume of target tissue in region 154 is exposed to a greater energy intensity, since the amount of tissue in proximity to the electrode arrays is increased by this compression.

When the first mode of operation is employed initially, the inner region 152 of the target tissue is predominantly affected by the RF energy applied by the electrode arrays 108, 110. Thus, after a desired degree of ablation of the tissue of the region 152 has been achieved, the impedance of the tissue region 152 increases, due to the desiccating effect of the RF energy. The increased tissue impedance reduces the ability of the RF energy to further penetrate through the desiccated tissue. To overcome this problem, the RF ablation device 100 is then switched to the second mode of operation wherein the outer region 154 of the target tissue mass 34 is predominantly affected by the RF energy. As the region 154 is affected by the RF energy to a much lesser extent while the device is operated in the first mode, after this first mode operation, the tissue in the region 154 is not yet desiccated and remains able to conduct electrical energy without excessive losses. A large volume of target tissue in the region 154 may thus be treated while the RF ablation device 100 operates in the second mode.

According to embodiments of the invention, the impedance of the tissue being treated by the RF ablation device 100 may be monitored to optimize the operation of the device. For example, the impedance of the region of tissue 152 between the electrode arrays 108, 110 may be monitored to determine when to switch from the first mode to the second mode of operation. When the impedance increases beyond a selected value, the electrode arrays 108, 110 are moved apart from one another, and the RF energy is preferentially applied to the tissue region 154. Further, the impedance of the tissue region 154 may be monitored, to discontinue the treatment when the impedance reaches a pre-selected threshold level. Feedback loop controls can be incorporated to control the switching between modes.

In the exemplary embodiment, one or more impedance sensors may be used to monitor the progress of the RF ablation treatment. For example, one or more sensors 160 may be incorporated in the shaft 106 to measure impedance within the target tissue mass 34. Alternatively, an external sensor probe 162 (see FIG. 11) may be inserted in the target tissue mass 34 to measure its impedance at various locations. A display 164 may be provided to notify the user of the impedance measured by the sensor(s), or may simply alert the user that a selected value of impedance has been reached. Display 164 may be part of the RF generator unit 112, or may be a separate unit independently connected to the sensor(s).

According to embodiments of the present invention, the operational sequence for the dual mode RF ablation device 100 comprises first inserting the shaft 106, with positive and negative electrodes 102, 104, into the target tissue mass 34 and then deploying the electrode arrays 108, 110 within the target tissue mass 34. After deployment in the target tissue mass 34, the electrode arrays 108, 110 are moved toward one another so that the portion 152 of the target tissue located therebetween is compressed. Electrical energy (e.g., RF energy) is then supplied to the arrays 108, 110 to ablate compressed tissue region 152. When a desired degree of ablation has been achieved, operation of the ablation device 100 is switched from the first mode to the second mode. Electric power supply to the arrays 108, 110 is suspended and the arrays 108, 100 are moved further apart so that they press against the surrounding region 154 of the target tissue mass 34. The application of energy is then resumed and is directed toward the tissue in the region 154 until a desired degree of ablation of the tissue is achieved.

Figure 14:
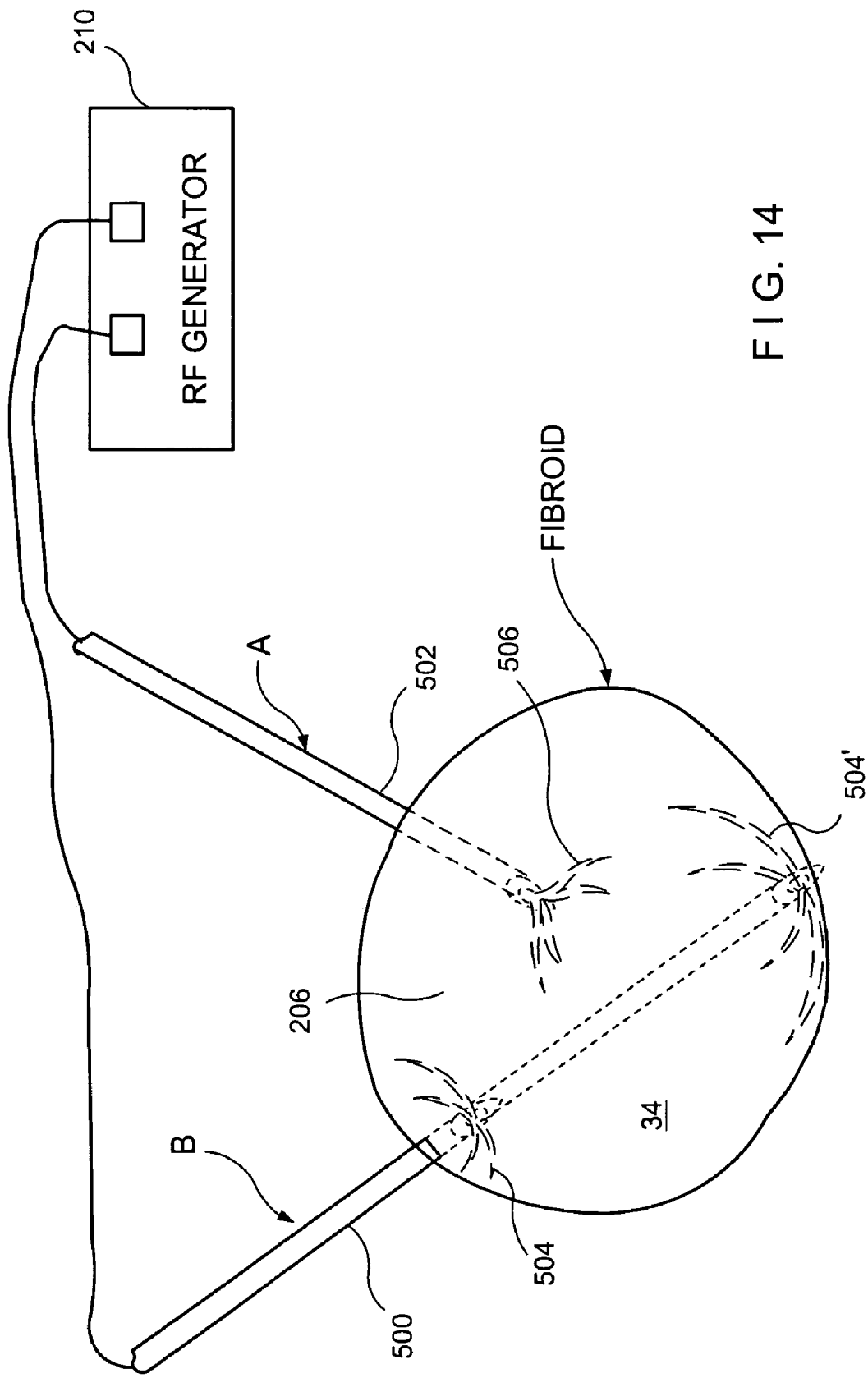
FIG. 14 shows a tissue ablation system according to a fourth embodiment of the invention.

A further exemplary embodiment is depicted in FIG. 14. In this case, elongated elements of the device are formed by needles 500, 502 which are not in a side by side layout. Instead, the needles 500 and 502 may be placed independently of one another in different places on or within the target tissue mass 34. For example, after the needle 500 has been inserted to a position 1 within the target tissue mass 34, the array of tines 504 is deployed near the surface of the target tissue mass 34, as described above. Alternatively, the surgeon may insert the needle 500 all the way to position 2 within the target tissue mass 34. The array of tines 504' may then be deployed near the surface of the target tissue mass 34 opposite the site of puncture of the target tissue mass 34. At the same time, the needle 502 may be inserted into the target tissue mass 34 from a different location and to a different depth. The area of tissue placed between the two electrodes defined by the arrays of tines 504, 506 may then be ablated by applying an electric voltage therebetween. Tumors of different sizes and tissue densities may be treated using this system, by adjusting the size and location of the array of tines 504, 506 and/or by performing a multi-step or compression dual mode ablation as described above.

Since the distance between the electrodes and the size and shape of the electrodes may be specified, damage to nearby organs can be minimized. Tumors of various sizes may be accommodated by the exemplary device, since the distance between the two electrodes can be changed by varying the extension of the needle 204 relative to the needle 202 and since the size of the arrays 206, 208 may also be controlled by the surgeon. The device according to the present embodiment is especially well suited for the treatment of fibroids, such as uterine fibroids, which are not homogeneous. Both of the arrays 206, 208 may be placed in contact with the surface of the target tissue mass 34 where most of the blood vessels feeding the target tissue mass 34 are located. As the impedance is lowest at this surface, the greatest flow of electricity and, thus, the greatest heat is generated here. The current thus tends to desiccate the surface layers and cauterize the blood vessels first, before the core of the fibroid is affected. This effect may be sufficient to cause the fibroid to die, without the need to completely ablate all of the tissue mass.

Figure 15:
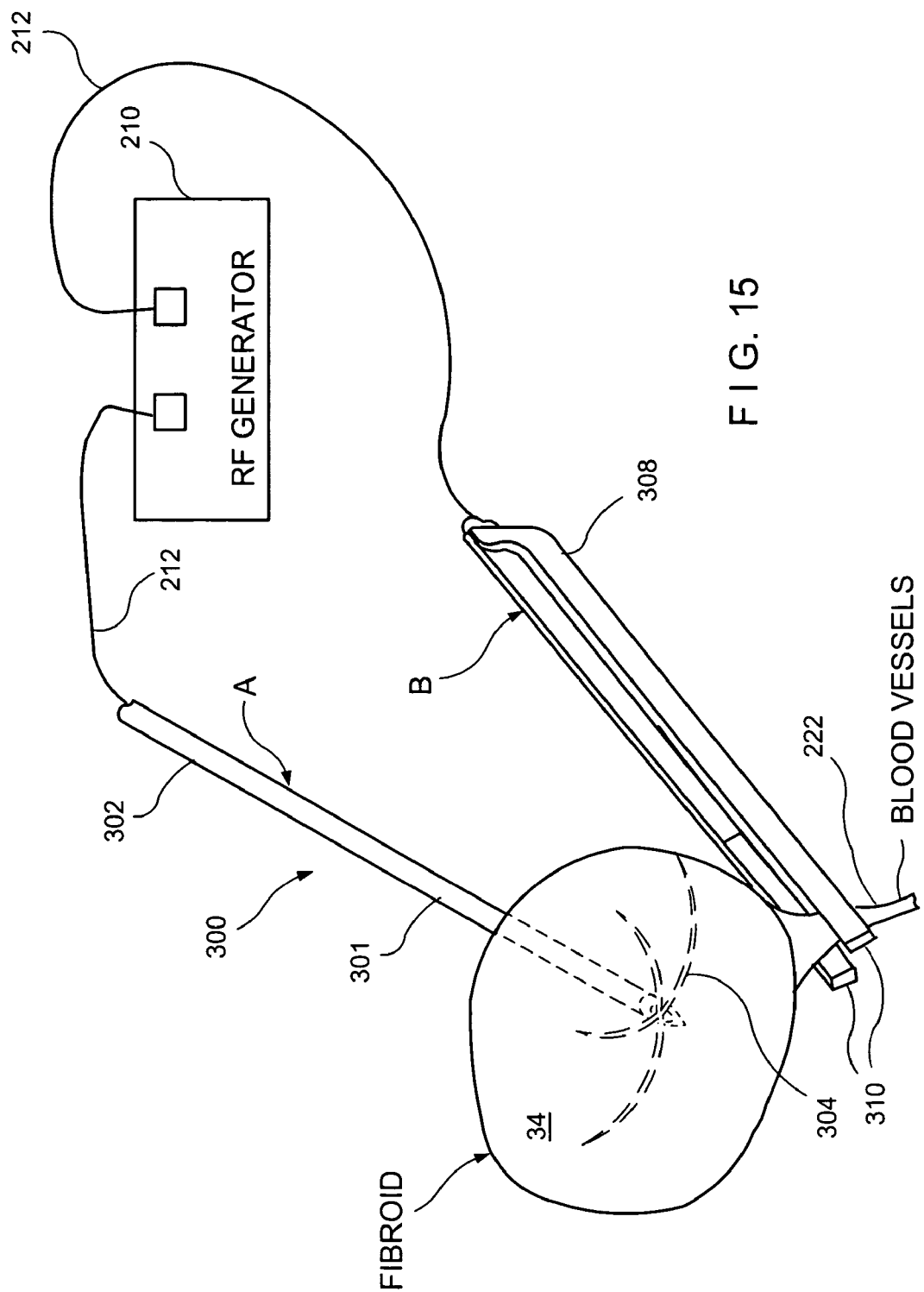
FIG. 15 shows the tissue ablation system according to a fifth embodiment of the invention.
Figure 16:
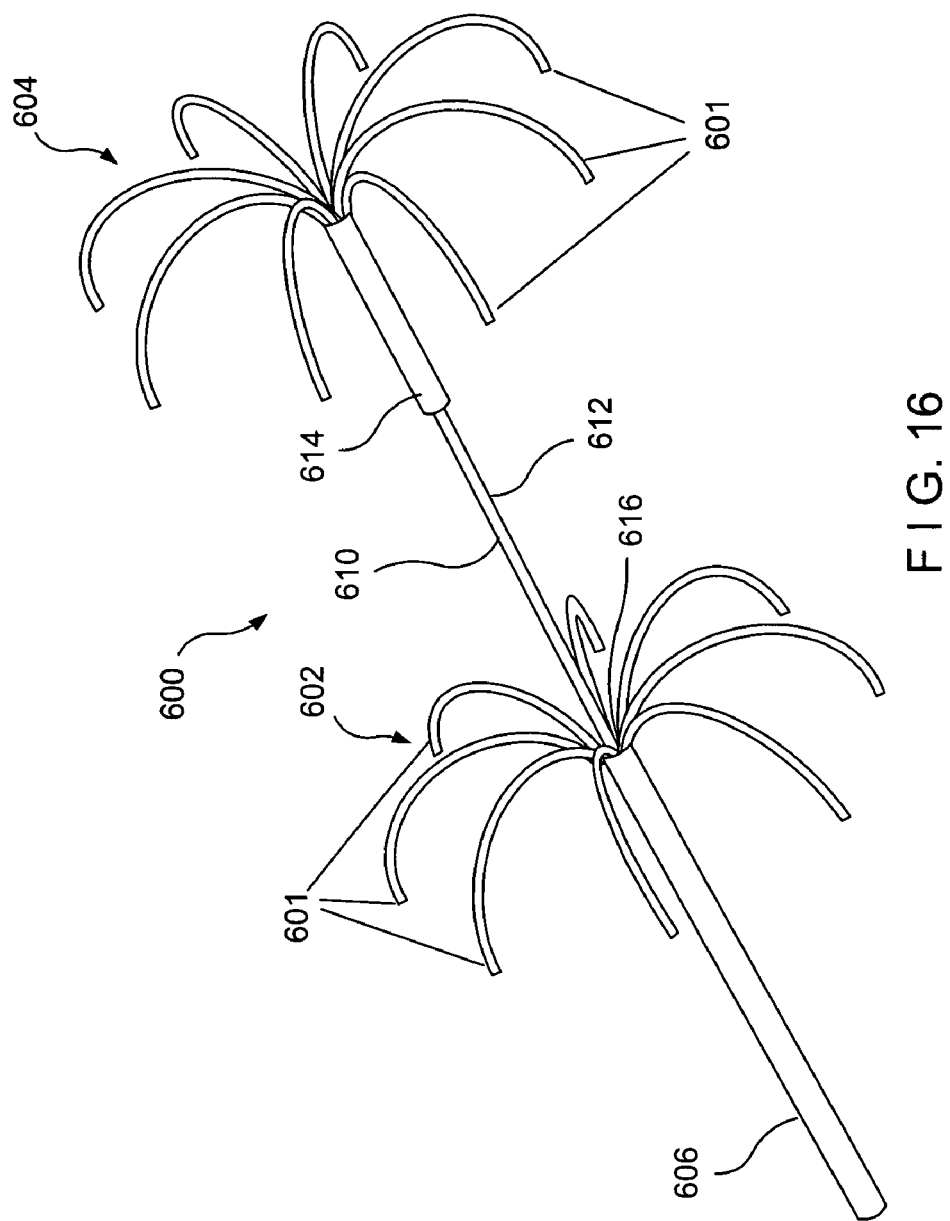
FIG. 16 shows a tissue ablation system according to a sixth embodiment of the invention.

FIG. 15 shows a different embodiment of the present invention, which includes a configuration specialized to cut off the blood supply to a target tissue mass 34 which may, for example, be a fibroid. The significant blood flow required by fibroids is provided by blood vessels that enter through the surface thereof. As discussed above, if the electrodes of the bipolar ablation system are located on the surface of the target tissue mass 34, this surface is the first part to be destroyed and any blood vessels thereon are cauterized.

According to this exemplary embodiment, a first electrode 301 comprising an elongated shaft or needle 302 is positioned in or on the target tissue mass 34. The first electrode 302 may be inserted into the target tissue mass 34 as shown in FIG. 15, or may be anchored to the surface of target tissue mass 34. In either case, an array of tines 304 is deployed from the hollow channel 306 into the mass or on the surface of the target tissue mass 34 with the specific details of the deployment of the first electrode 301 varying depending on the type and location of the target tissue mass 34. It will be apparent to those of skill in the art that other configurations of the first electrode 301 may be utilized without departing from the scope of the invention.

A second electrode 308 may be placed directly on, or in close proximity to a blood vessel 222 feeding the target tissue mass 34. For example, the second electrode 308 may comprise a pair of clamping arms 310 which may be clamped on or near the blood vessel 222. With this configuration of electrodes the least impedance is found near the blood vessel 222, which is heated by the current flowing from electrode 308 and is eventually cauterized. As in the previously described embodiment, a generator 210 may be connected to first and second electrodes 301, 308 via electric connections 212. The specific configuration of the electrodes may be varied depending on the type of tumor being treated. For example, the second electrode 308 may be designed to fit through an incision made to reach the blood vessel feeding the target tissue mass 34. Various configurations of the clamping arms 310 may be used also depending on the shape and location of the target tissue mass 34. Similarly, different configurations of first electrode 301 may be used, according to the procedure being carried out.

As indicated above, a conventional power supply 210 may be used to provide a voltage between the electrodes to induce a current through the tissue located therebetween. A handle may also be provided at the proximal end of the device to permit the surgeon to manipulate the insertion needles and the arrays of tines used in the exemplary embodiments of the invention described herein. For example, the insertion needles used to reach the target tissue mass may be manipulated directly by the surgeon, and may include at the proximal end a sliding control lever or other conventional device adapted to cause the deployment of the arrays of tines from said insertion needles. Those of skill in the art will understand that the specific details of the control and guidance mechanisms used in conjunction with the present invention will vary depending on the surgical procedure being carried out.

A bi-polar ablation device 600 according to a further embodiment of the invention is shown in FIGS. 16-20. The device 600 includes first and second sets of electrodes 601 formed in proximal and distal arrays 602, 604, respectively, which are moveable relative to one another along an axis of a cannula 606. The arrays 602 and 604 are substantially similar to one another with the electrodes of each array extending distally away from the cannula 606 and curving back to face proximally with ends of the electrodes of each of the arrays 602, 604 positioned along circles of substantially equal diameters. The proximal array 602 is bonded, e.g., butt welded, to a distal end of a tube 608 slidably received within the cannula 606 and the distal array 604 is bonded to a mandrill 610 which is slidably received within a lumen of the tube 608. The mandrill 610 includes a reduced diameter portion 612 so that, when the proximal array 602 is in a folded configuration received within the cannula 606, the electrodes of the proximal array 602 may be folded sufficiently to maintain an outer diameter of the folded array 602 substantially equal to an outer diameter of the tube 608. This allows an inner diameter of a lumen of the cannula 606 to be minimized, thereby minimizing an outer diameter of the cannula 606. Those skilled in the art will understand that minimizing the outer diameter of the cannula 606 reduces the size of puncture required to introduce the device 600 into the body to a target portion of tissue, thereby reducing patient discomfort.

The distal array 604 includes a cylindrical portion 614 bonded to the mandrill 610 with the electrodes 601 separating from one another at a distal end of the cylindrical portion 614. The outer diameter of the mandrill 610 and the outer diameter of the cylindrical portion 614 are preferably insulated so that energy is not transferred therefrom to tissue. The insulation completely covers the entire length of the mandrill 610 and electrically insulates the electrodes 601 of the arrays 602, 604 from one another when they are in a working position (open). The insulation preferably extends from the outer diameter of the mandrill 610 and the cylindrical portion 614 along portions of the surfaces of the electrodes 601 from which it is not desired to transfer energy to tissue. Those skilled in the art will understand that the insulated portion of the electrodes 601 may be varied from a tips-only configuration where only distal tips of the electrodes 601 of the array 604 are uninsulated to transfer energy therefrom to tissue to a full electrode configuration where entire lengths of the electrodes 601 of the distal array 604 are uninsulated to transfer energy to tissue from a larger surface area. Those skilled in the art will further recognize that the uninsulated portions of the electrodes 601 may be varied in any manner desired to achieve desired ablation properties.

In addition, an inner diameter of the cannula 606 is preferably uninsulated to minimize the overall diameter of the device. In a folded position, the arrays 602, 604 are electrically coupled to one another through the cannula, but as soon as the distal array 604 is out of the cannula 606, the arrays 602, 604 are electrically de-coupled from one another.

In use, the ablation device 600 is initially configured with both arrays 602, 604 folded radially inward within the cannula 606. In this configuration, the tube 608 and the mandril 610 preferably project from a proximal end of the cannula 606 so that they are accessible to the user during use of the device. Electrical energy is preferably supplied to the arrays 602, 604 via the tube 608 and the mandrill 610, respectively, so these elements are preferably formed of an electrically conductive material with an insulated grasping portion or handle (not shown) at proximal ends thereof. The cannula 606 is advanced into the body until a tissue penetrating distal tip 616 thereof is positioned at a location in which it is desired to deploy the distal array 604. Those skilled in the art will understand that this positioning may be done using known visualization techniques in a manner similar to that used, for example, in positioning conventional needle ablation devices. Once the tip 616 is in the desired position for deployment of the distal array 604, the user grasps the proximal end of the mandrill 610 and moves it distally into the cannula 606 while maintaining the position of the tube 608 constant relative to the cannula 606 until the cylindrical portion 614 of the array 604 clears the tip 616. As the electrodes 601 of the array 604 are biased toward the deployed configuration shown in FIG. 16, they spring out into the deployed configuration as they clear the tip 616. The user then draws the cannula 606 with the tube 608 proximally along the mandrill 610 keeping the position of the array 604 constant until the tip 616 is in a position for deployment of the proximal array 602. The user then draws the cannula 606 proximally relative to the tube 608 while maintaining the position of the distal array 604 constant until the electrodes 601 of the proximal array 602 deploy under their bias to the deployed configuration. Those skilled in the art will understand that, up to the point where the proximal array 602 deploys, the user may adjust the relative positions of the arrays by sliding the tube 608 relative to the mandrill 610 until a desired separation between the arrays is obtained.

Those skilled in the art will further understand that distance by which the arrays 602, 604 are separated may be monitored, for example, by observing markings on the proximal ends of the tube 608 and the mandrill 610 or using the visualization techniques. This allows the user to select a desired separation distance for a single application ablation or to vary the distance between the arrays 602, 604 to perform the multi-stage ablation as described above. Specifically, to move the arrays 602, 604 after an initial ablation stage has been completed, the cannula 606 is advanced distally over the arrays 602, 604 until the tips of the electrodes 601 of the array 604 are received therewithin and the tip 616 of the cannula 606 is moved to the desired position for deployment of the distal array 604, the distal array 604 is deployed and then the proximal array is deployed in its desired position in the same manner described above for the initial positioning of the arrays 602, 604.

An exemplary method for making an array of electrodes as described above in regard to FIGS. 16-20, begins with a sheet 620 of suitable metal (e.g., Stainless Steel 455) as shown in FIGS. 21 and 22. Those skilled in the art will understand that any biocompatible, electrically conductive material may be used so long as the mechanical properties of the material are suitable to the introduction of a bias to the desired deployed configuration sufficient to move the array to the desired position overcoming the resistance of the tissue. The sheet 620 is cut to a desired shape with a length $L_1$ of the sheet being equal to a length $L_2$ of the electrodes 601 plus a length $L_3$ of the cylindrical portion 614. Those skilled in the art will understand that the sheet 620 may be cut by grinding, laser cut, stamping, sharing or any other suitable method. A width W of the sheet is substantially equal to a circumference of the cylindrical portion 614. The sheet 620 is then sliced from a distal end thereof along a plurality of lines 622 of length $L_2$ to separate the electrodes 601 from one another. As shown in FIG. 22, the distal portion of the sheet 620 defining the electrodes 601 is then bent into the desired shape to which the electrodes 601 are to deploy when moved out of the cannula 606. As shown in FIG. 18, the sheet 620 is then rolled about an axis substantially centered along the width of the sheet 620 and separated from a surface thereof by a distance substantially equal to $W/2\pi$ and fixed in this position (e.g., by welding) to create the array. The portion of the sheet 620 extending proximally from the proximal ends of the lines 622 forms the cylindrical portion 614 of the array.

In addition, the sheet 620 may be cut, for example, by stamping a thickness of each of the electrodes 601 along its length and may be varied to adjust a rigidity of the electrodes 601 along its length. The arrays 602, 604 may be made identically with the array 602 being coupled to the tube 608 (e.g., via butt welding) while the cylindrical portion 614 of the distal array 604 is coupled to the mandrill 610 by, for example, spot or laser welding.

Figure 23:
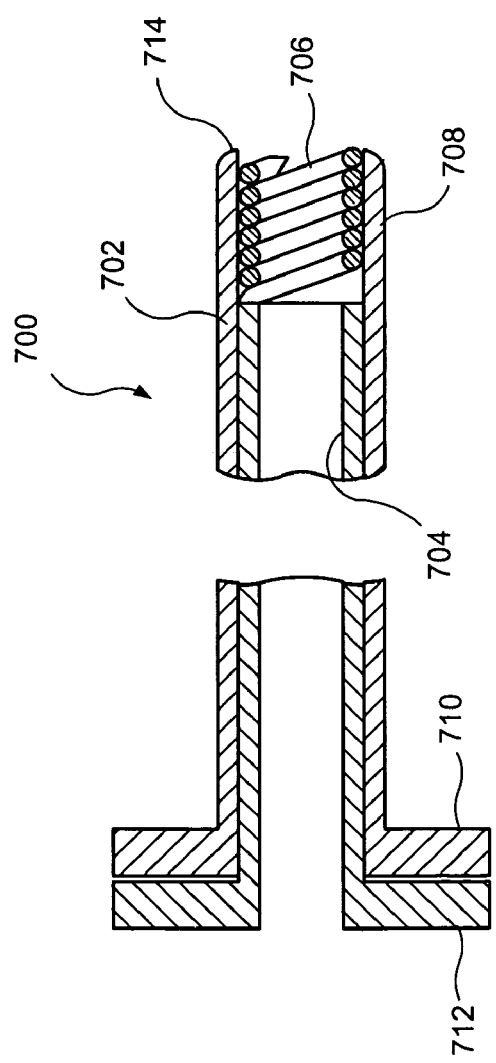
FIG. 23 shows a side elevation view of an anchoring device according to an embodiment of the invention.

According to other exemplary embodiments of the present invention, a fibroid anchoring device is provided having a diameter dimension which may be increased once the anchoring device has been placed at a desired location within the body. The result is to maximize a ratio of diameter to length of the anchoring device, to better apply a traction force to the fibroid during surgery while reducing the chance of the fibroid slipping from the device. FIG. 23 shows an exemplary embodiment of this aspect of the invention in a collapsed configuration, constrained within a sheath. The exemplary device is formed of two substantially concentric tubes 702, 704 one slightly smaller in diameter than the other. The tubes 702, 704 may be made of a biocompatible material and is more preferably made of a biocompatible metal such as stainless steel, or other materials that is also electrically conductive.

Figure 24:
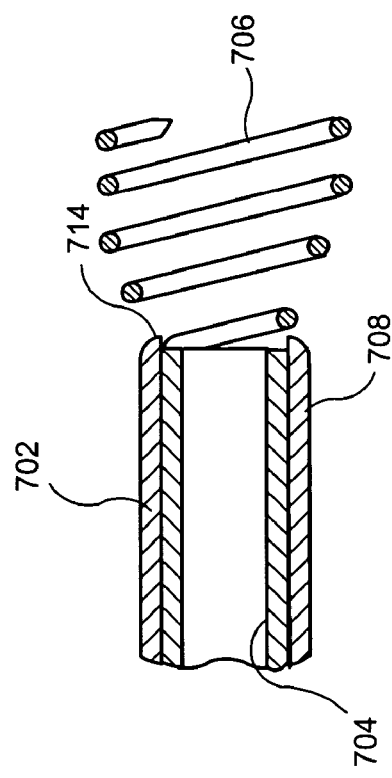
FIG. 24 shows a side elevation view of the anchoring device of FIG. 23 in a deployed configuration.

A screw or coil-like assembly 706 is disposed at a distal end of the inner tube 704, which has a smaller diameter than the tube 702. The inner tube 704 is rotatable and slidable within the outer tube 702, and may be easily manipulated using handles 710 and 712 located at the proximal end of the device 700. The inner tube 704 is translated slidably distally to deploy the screw coil 706 and may be pulled proximally to retract the coil 706. The inner tube 704 may be rotated using the handle 712 to screw the coil 706 into a target portion of tissue. The coil 706 is preferably formed from a material that is sufficiently flexible to allow it to collapse in diameter when it is pulled inside of the outer tube 702 and to expand to a larger diameter when deployed beyond the distal end 714 of the outer tube 702. FIG. 23 shows an embodiment of the tissue anchoring device 700 according to the invention in the collapsed configuration, constrained within the outer tube 702. FIG. 24 shows the distal end of the same tissue anchoring device 700 with the coil 706 deployed outside of the distal end 714 of the outer tube 702.

The dimensions of the coil 706 may be varied from a smaller diameter at a proximal end thereof while the coil 706 is constrained within the outer tube 702 to a larger diameter when the coil 706 is pushed outside of the distal portion 708 of the outer tube 702, beyond the distal end 714 thereof. In this manner the proximal retraction of the coil 706 back within the distal portion 708 is accomplished by pulling the inner tube 704 proximally while simultaneously rotating it using the handle 712 to screw the coil 706 back into the distal portion 708. Deployment of the coil 706 is accomplished by pushing the inner tube 704 distally using the handle 712, while retaining the outer tube 708 in place by holding the handle 710. The handle 712 is rotated to "screw" the coil 706 into the target portion of tissue. When the coil 706 is deployed, the increased ratio of the diameter of the coil 706 to its length results in better traction of the tissue into which the coil 706 is screwed.

In one exemplary embodiment, the coil 706 is made of a shape memory alloy such as Nitinol. As would be understood by those skilled in the art, if the coil 706 is to be used as an electrode of a bipolar ablation system, it will be made of an electrically conductive material. As described above, the coil 706 may be simply an elastic member that returns to an expanded configuration when it is no longer mechanically constrained by an element such as the outer tube 702. Alternatively, the coil 706 may utilize shape memory properties of the material of which it is formed (e.g., Nitinol) to expand due to a temperature increase. For example, the coil 706 may retain the reduced diameter configuration shown in FIG. 5 at room temperature, but may expand to the greater diameter configuration shown in FIG. 6 as it warms to body temperature. In cases where the temperature sensitivity of a shape memory alloy is utilized, it may not be necessary to mechanically constrain the coil 706 and outer tube 702 may be at least partially omitted.

Figure 25:
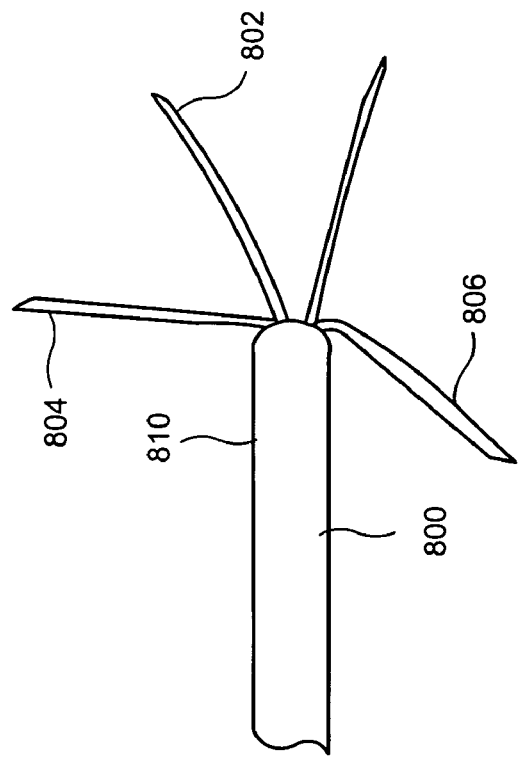
FIG. 25 shows an anchoring device according to a further embodiment of the invention.

Alternate embodiments of the present invention may include an array of tines designed to be deployed from a distal end of an insertion tube. For example, as shown in FIG. 25, a needle like insertion tube 800 which may be formed as a needle comprises a hollow core from which the array of tines 802 is deployed through the manipulation of a conventional handle at a proximal end of the device. After a distal tip 810 of the tube 800 punctures the target portion of tissue (e.g., a fibroid), the array of tines 802 is deployed into the tissue to stabilize or retract the target portion of tissue. In a different embodiment, an array of arms or tines 804 may be deployed from the tube 800 in a direction substantially perpendicular to the tube 800 to increase the traction capability compared to the array of tines 802. In yet another embodiment, an array of tines 806 may be deployed from the tube 800 extending proximally from the distal end 810 at an acute angle relative to the tube 800. This latter configuration may provide an even greater amount of traction to the tumor, with less chance of the tissue slipping from the device.

The internal mechanisms of the exemplary embodiments shown in FIG. 25 may be conventional, and may comprise more or less complex mechanisms depending on the orientation of the tines after deployment. All the described embodiments of the tumor stabilization and traction devices may form a first electrode of a bipolar RF ablation device, as described above. However, the tumor traction and stabilization functions may also be carried out independently by devices employed simply as tumor screws. The needle or tube insertion devices described above may preferably be formed of biocompatible metals such as stainless steel or nitinol, but also may be made from rigid plastics such as polycarbonate, ABS, polyimide, or other similar materials.

The present invention has been described with reference to specific exemplary embodiments. Those skilled in the art will understand that changes may be made in details, particularly in matters of shape, size, material and arrangement of parts. As would be understood by those skilled in the art, the various devices according to the present invention allow larger target tissue masses to be ablated with only a single puncture in the tissue mass and/or with reduced punctures in the abdominal and uterine wall (in the case of percutaneous access), reducing bleeding and, consequently, lowering the risk of adhesion. In addition, the flexibility of electrode positioning and the described ablation methods allow a single device to be used to ablate target tissue masses in a wide size range with the ability to ablate larger tissue masses than for comparably sized devices. Accordingly, various modifications and changes may be made to the embodiments. Additional or fewer components may be used, depending on the condition that is being treated by the neurostimulation system. The specifications and drawings are, therefore, to be regarded in an illustrative rather than a restrictive sense.

What is claimed is:

1. A method of ablating body tissue, comprising:
    inserting first and second electrodes into a body to desired initial positions relative to a tissue mass to be ablated;
    applying electrical energy between the first and second electrodes to thereby ablate a first portion of the tissue mass located between the first and second electrodes;
    moving the first and second electrodes to respective second and third positions in the body outside of the initial positions;
    applying electrical energy between the first and second electrodes while located at the respective second and third positions to thereby ablate a second portion of tissue surrounding the first portion of tissue.

2. The method of claim 1, further comprising the steps of, before ablating the first portion of tissue, deploying the first and second electrodes into tissue and the moving the first and second electrodes toward one another to compress the first portion of tissue.

3. The method according to claim 1, further comprising the step of, after ablating the first portion of tissue, moving the first and second electrodes to the desired second and third positions.

4. The method according to claim 1, further comprising the step of, after ablating the first portion of tissue, energizing at least one third electrode separated from both the first and second electrodes, to ablate the second portion of tissue.

5. The method according to claim 4, wherein the step of energizing at least one third electrode includes energizing a fourth electrode separate from the first, second and third electrodes to ablate the second portion of tissue.

6. The method according to claim 5, wherein the first, second, third and fourth electrodes are mounted on an elongated member with the first and second electrodes being located between the third and fourth electrodes.

7. The method according to claim 1, wherein one of the first and second electrodes comprises an array of tines.

8. The method according to claim 1, further comprising measuring an impedance of tissue to determine when a desired degree of ablation has been achieved.

9. The method according to claim 8, further comprising terminating the application of electrical energy to the first portion of tissue when the impedance thereof exceeds a first predetermined value.

10. The method according to claim 1, wherein the step of moving at least one of the first and second electrodes away from the other of the first and second electrodes includes moving both the first and second electrodes substantially equal distances from a centerline midway therebetween to substantially center the first portion of tissue therebetween.

11. The method according to claim 1, wherein a distance between the first and second electrodes before application of electrical energy to the first portion of tissue is selected so that a diameter of the first portion of tissue is a maximum along a centerline midway between the first and second electrodes.

12. The method according to claim 1, wherein energy is applied to the second positions only after the first portion of tissue to be ablated has been ablated.

13. The method according to claim 1, wherein the second and third positions are in a surrounding relationship to, the first ablated portion of tissue.

14. The method according to claim 1, wherein the initial, second, and third positions are aligned.

* * * * *